(12) United States Patent
Taneja et al.

(10) Patent No.: US 7,057,040 B2
(45) Date of Patent: Jun. 6, 2006

(54) SUBSTITUTED ARYL ALKENOIC ACID HETEROCYCLIC AMIDES

(75) Inventors: Subhash Chandra Taneja, Jammu (IN); Surrinder Koul, Jammu (IN); Jawahir Lal Koul, Jammu (IN); Beenu Moza, Jammu (IN); Sukhdev Swami Handa, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/067,546

(22) Filed: Feb. 7, 2002

(65) Prior Publication Data

US 2003/0161860 A1    Aug. 28, 2003

(51) Int. Cl.
*C07D 295/192*   (2006.01)
(52) U.S. Cl. ............ 544/176; 544/148; 544/151; 544/174; 544/377; 544/386
(58) Field of Classification Search ............ 544/174, 544/148, 151, 377, 386, 176
See application file for complete search history.

(56) References Cited

U.S. PATENT DOCUMENTS 4,209,445 A * 6/1980 Oediger et al. ............ 540/596
6,008,376 A * 12/1999 Sharpless et al. ........... 548/965
6,346,539 B1 * 2/2002 Raman et al. ............... 514/321

OTHER PUBLICATIONS

Explore Library Collection (Sep. 18, 2000)—see CA Registry No. 321689-62-7.*
CA Registry No. 349578-28-5, entry date into the CAS Registry file is Jul. 31, 2001.*
Do et al., CA 107:39671, 1987.*
Puscaru et al., CA 56:38494, 1962.*

* cited by examiner

*Primary Examiner*—Laura L. Stockton
(74) *Attorney, Agent, or Firm*—Nath & Associates PLLC; Harold L. Novick; Lee C. Heiman

(57) ABSTRACT

The present invention relates to novel compounds possessing specific hot, pungent and spicy taste when subjected to direct pungency evaluation, which may be useful as food additives and anti-oxidants, however the said compounds do not add to any nutritional value but the synthesised compounds can possess useful pharmacological properties which is expected to find application in new test models for the development of anti-inflammatory drugs, bioavailability enhancers and for the study of hepatic drug metabolising mechanism; also relates to a process for preparing the said compounds.

1 Claim, No Drawings

SUBSTITUTED ARYL ALKENOIC ACID HETEROCYCLIC AMIDES

FIELD OF THE INVENTION

The present invention relates to novel substituted aryl alkenoic acid heterocyclic amides. The invention particularly relates to the novel substituted aryl alkenoic acid heterocyclic amides of general formula 1, useful as food additives and in pharmaceutical applications:

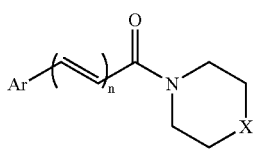

1 wherein n=1 or 2, X=O or N—CH$_3$ and

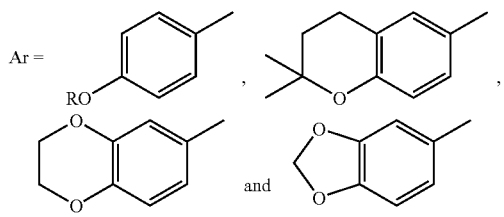

wherein R=linear or branched C$_1$ to C$_5$ alkyl chain

BACKGROUND OF THE INVENTION

Aroma, flavour and taste are considered to be the three important parameters for determining the quality of spices or condiments. The aroma and flavour of a spice depends upon the presence of volatile components, which are perceived through the olfactory epithelium present in the nose. The olfactory substances are primarily mono-, sesqui- or diterpenes, low molecular weight hydrocarbons, heteroacyclic or heterocyclic compounds. The taste is perceived by the taste buds present on the surface of the tongue. The interactions between the pungent molecules and receptors present on the surface of the tongue are the main cause of generation of hot sensation or thermogenecity which is associated with pungency. More pungent the substance, more is the duration of the feeling of hotness. This feeling of hotness may also be perceived on other tender parts of the skin. Most of the known natural pungent substances are aromatic in nature. Some of the most commonly known natural pungent substances include piperamides such as piperine from black pepper (*Piper nigrum*), capsaicinoids such as capsaicin and dihydro-capsaicin from red chillies (*Capsicum annum*) and gingeroids like gingerol from ginger (*Zingiber officianalis*) etc. The chemistry and properties of pungent compounds from natural sources has recently been reviewed (Nakatani, Nobugi; Koryo, 1995, 185, p 59–64, *Chem. Abs.* 123, 5520 n).

These pungent principles which possess anti-oxidant properties are also associated with many physiological actions viz piperamides, capsaicinoids as well as gingeroids are reported to possess anti-inflammatory properties (Lewis, D. A. in Anti-inflammatory drugs from plant and marine sources; Birkhauser Verlag, Berlin, 1989, p 216–220; Janusz, J. M., *J. Med. Chem.* 1993, 36, p 2595). Both piperine and dihydrocapsaicin were found to interact irreversibly with hepatic drug metabolizing enzymes thereby inhibiting their activity as indicated by prolongation of pentobarbital sleeping time in rats (Sush Young-Joon, A, et al., *Life sciences*, 1995, 56(16), p 305–31 1; Atal, C. K. et al., *J. Pharmacol. Exp. Therp.* 1985, 232, p 258–262).

Only few reports have appeared in the literature related to the evaluation of structure with respect to pungency. Wilbur Scoville developed direct subjective method of analysis of capsaicin and related extracts for their pungency evaluation in 1912. In this method potency of pepper was measured as heat units by diluting the extracts until pungency was just detected after placing a drop on the tongue. Pure capsaicin was thus assigned $10^7$ units and jalapeno $10^3$ units (Scoville, W. J., *Am. Pharm. Assoc.* 1912, 1, p 453–454). Indirect evaluations of pungency through the measurement of physiological effects have also been employed. For example Watnabe et al. reported the assessment of pungency related thermogenecity to structure of capsaicin analogues by correlating it with adrenal catecholamine secretion in rats (Watnabe, Tatsno et al. *Life. Sci.*, 1994, 54(5), p 369–374; *Chem. Abs.*, 120: 94792f). Astringent and pungent substances were studied using a multichannel taste sensor by observing the changes in electric potential in lipid membranes. However pungent substances were found to have no effect on the membrane potentials (Iiyama, Satoru et al., *Chem. Senses*, 1994, 19(1), p 87–96; *Chem. Abs.* 120: 295156).

Known natural or synthetic pungent substances are invariably oxygenated aromatic compounds with an alkyl side chain and a heteroatom comprising preferably an amide linkage in the side chain. Some of these compounds were found to possess hot pungent characteristics on preliminary evaluation. On the basis of above observation several new series of aryl alkenoic acid amides were synthesised and their structure and pungency relationship has also been established. Another important aspect of the development of these compounds is the possibility of their utilisation as new test models for the study and management of the phenomenon of pain and inflammation. These observations are based on the recent work carried out by the David Julius et al. who have identified the capsaicin receptor by isolating the complimentary DNA encoding the binding protein (Julius, D. et al. *Nature*, 1997, 389, p 816–824). Isolation and identification of the receptor protein is an important development for the study of new pharmacological targets which will help in understanding the phenomenon of chronic pain caused by arthritis, spinal cord injury or diabetic neuropathy. It is expected that vanilloid receptor and the receptor for the synthesised compounds of general formula 1 may turn out to be the same. Therefore, the development of these novel compounds may provide a diverse and effective alternate to capsaicin and related vanilloids.

OBJECTS OF THE INVENTION

The main object of the present invention is to provide the novel substituted aryl alkenoic acid heterocyclic amides.

Another object of the present invention is to provide an economical and effective process for the preparation of aryl alkenoic acid heterocyclic amides of general formal I.

Still another object of the present invention is to provide novel synthetic compounds useful as thermogenic, pungent and spicy agents.

Yet another object of the present invention is to provide novel compounds which can find application as new test models for the development of anti-inflammatory drugs, bioavailability enhancers and for the study of hepatic drug metabolising mechanism.

Still yet another object of the invention is to provide novel aryl alkenoic acid heterocyclic amides of general formula 1 which may be useful as hot, pungent and spicy agents, and also as food additives, anti-oxidants, bioavailability enhancers and for the study of hepatic drug metabolising mechanism including UDP-glucose dehydrogenase and glucuronidation activities.

SUMMARY OF THE INVENTION

The compounds of this invention are all novel and possess specific hot, pungent and spicy taste when subjected to direct pungency evaluation. The compounds of the present invention do not add to any nutritional value. These compounds may be useful as food additives and anti-oxidants. The synthesised compounds can possess useful pharmacological properties which is expected to find application in new test models for the development of anti-inflammatory drugs, bioavailability enhancers and for the study of hepatic drug metabolising mechanism.

Accordingly, the present invention provides a process for the preparation of novel aryl alkenoic acid heterocyclic amide of general formula 1, wherein n, x, Ar and R have the same definition as mentioned earlier

DETAILED DESCRIPTION OF THE INVENTION

In accordance, the present invention provides a process for the preparation of aryl alkenoic acid heterocyclic amide of general formula 1, useful as food additives and in pharmaceutical applications, said process comprises steps of:

(a) reacting aldehyde of general formula (5) with alkyl magnesium halide with constant stirring at ambient temperature in an anhydrous ethereal solvent to produce corresponding phenyl ethanol of general formula (4),

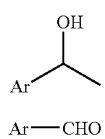

4

Ar—CHO  5

(b) treating the compound of general formula (4) with dimethyl formamide and phosphorous oxychloride at 0° to 10° C. for 20–40 hours, working up the reaction mixture by adjusting the pH of the solution and isolating the product of general formula (3) by using conventional method,

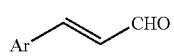

3

(c) reacting the compound of general formula (3) with witting reagent in presence of a base at a temperature range of 15–80° C. in an ethereal solvent for a period of 1–80 hours to get the corresponding carboxylic ester, (d) hydrolysing the ester of step (c) with strong alkali solution followed by acidification of the reaction mixture to produce the corresponding carboxylic acid of general formula (2),

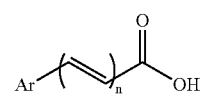

2

(e) reacting compound of step (d) having general formula (2) with thionylychloride in presence of an organic solvent at a temperature range of 70° C.–80° C., removing the solvent to obtain the corresponding acid chloride, (f) reacting the acid chloride of step (e) with heterocyclic amine in presence of an inert organic solvent at a temperature range of 0 to 50° C. for 1 to 16 hours, isolating the product of general formula 1 by purifying the reaction mixture.

In an embodiment of the present invention, the alkyl magnesium halide used is methyl magnesium iodide.

In another embodiment, the ethereal solvent used is selected from group consisting of diethyl ether and tetrahydrofuran and preferably tetrahydrofuran.

In yet another embodiment, the solution of the reaction mixture is adjusted to pH 6 to 8 to isolate the required intermediate product.

In still yet another embodiment, the product after preadjustment of pH is isolated by either filtration or extraction with organic solvent selected from a group consisting of ethylacetate, chloroform, dichloromethane and dichloroethane.

In still another embodiment, the witting reagent used is prepared from the reaction of equimolar mixture of triphenyl phosphine and bromomethyl acetate or bromoethylacetate.

In still further embodiment, the alkali used for hydrolysis is selected from the group consisting of sodium hydroxide, potassium hydroxide and calcium hydroxide.

In yet another embodiment, the acidification of the reaction mixture is performed using sulfuric acid or hydrochloric acid.

In still another embodiment, the condensation of acid chloride and hetrocyclic amine is carried out in an organic solvent selected from the group consisting of benzene, toluene, dichloromethane and ethyl acetate and preferably dichloromethane.

In a further embodiment wherein, purification of the product is carried out by employing crystallization or column chromatography technique.

In yet another embodiment, the novel aryl alkenoic acid amide compounds prepared can be used as best models for the study and management phenomenon of ailments like pain and inflammation.

In a further embodiment, the novel aryl alkenoic acid amide compounds can be used as best models for the development of inflammatory drugs, bioavailability enhancers and also for the study of hepatic drug metabolic mechanism.

The compounds of above invention were assessed in terms of the heat units for ascertaining their potency, by a panel of five untrained volunteers through a subjective or direct analysis using modified W. Scoville method. A stock solution of the compound (1%) in alcohol: water (1:1) was diluted until the sensation of pungency/hotness just detected by placing 5 μl of the solution on the tip of the tongue of the volunteers. In all the cases the pungency measurement was made in the reverse order i.e. from less dilute to more dilute solutions till pungency detection was just possible. Mouth and tongue were thoroughly washed with water after each evaluation, sufficient time gap was given before the next evaluation was initiated. In most of the compounds a clear solution was obtained in stock solutions. In some cases where solubility was poor, a uniform suspension was prepared through magnetic stirring or sonication. Although individual perception of pungency varied from person to person, on an average fair consistency was achieved.

Structure and pungency index of some of the representative compounds of general formula 1

| S. No | Structure | M. F. | M. P. ° C. | Pungency index |
|---|---|---|---|---|
| i | 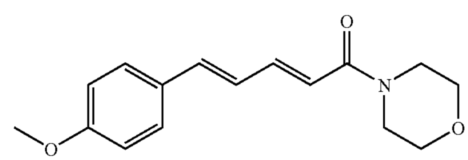 | $C_{16}H_{19}NO_3$ | 133 | $10^6$ |
| ii | 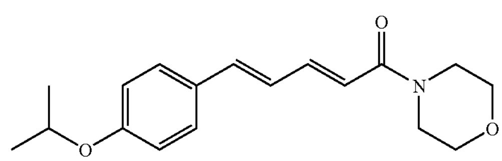 | $C_{18}H_{23}NO_3$ | 134 | $10^7$ |
| iii | 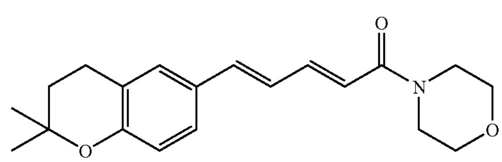 | $C_{20}H_{25}NO_3$ | 171 | $10^4$ |
| iv | 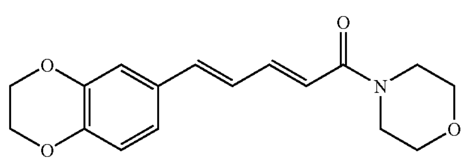 | $C_{17}H_{19}NO_4$ | 137 | $10^4$ |
| v | 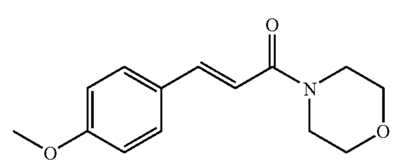 | $C_{14}H_{17}NO_3$ | 95 | $10^5$ |
| vi | 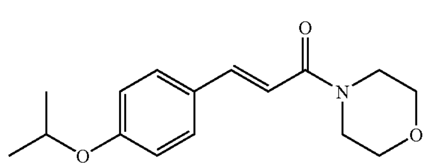 | $C_{16}H_{21}NO_3$ | 98 | $10^6$ |
| vii | 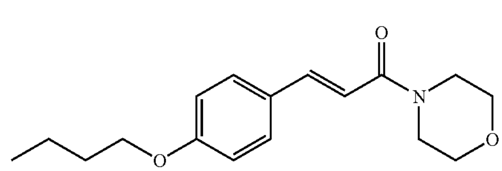 | $C_{18}H_{23}NO_3$ | 117 | $10^7$ |

-continued

Structure and pungency index of some of the representative compounds of general formula 1

| | | | | |
|---|---|---|---|---|
| viii | (structure) | $C_{17}H_{23}NO_3$ | 70 | $10^4$ |
| ix | (structure) | $C_{16}H_{19}NO_3$ | 88 | $10^6$ |
| x | (structure) | $C_{15}H_{17}NO_4$ | 139 | $10^4$ |

| Compound No. | Compound Name |
|---|---|
| i) | 5-(4-methoxy phenyl)-2E,4E-pentadienoic acid morpholine amide |
| ii) | 5-(4-isopropyloxy phenyl)-2E,4E-pentadienoic acid morpholine amide |
| iii) | 5-(2H)-2,2-dimethyl-3,4-dihydro-benzopyran-6yl-2E,4E-pentadienoic acid morpholine amide |
| iv) | 5-(3,4-ethylenedioxy phenyl)-2E,4E-pentadienoic acid morpholine amide |
| v) | 3-(4-methoxy phenyl)-2E-propenoic acid morpholine amide |
| vi) | 3-(4-isopropyloxy phenyl)-2E-propenoic acid morpholine amide |
| vii) | 3-(4-butyloxy phenyl)-2E-propenoic acid morpholine amide |
| viii) | 3-(4-allyloxy phenyl)-2E-propenoic acid morpholine amide |
| ix) | 3-[(2H)-2,2-dimethyl-3,4-dihydro-benzopyran-6yl]-2E-propenoic acid morpholine amide |
| x) | 3-(3,4-ethylenedioxy phenyl)-2E-propenoic acid morpholine amide |

Pungency index of reference compounds

| | | | | |
|---|---|---|---|---|
| A | (structure) Piperine | $C_{17}H_{19}NO_3$ | 130 | $10^4$ |
| B | (structure) Dihydrocapsaicin | $C_{18}H_{29}NO_3$ | — | $10^6$ |

The invention is illustrated with the following examples, which should not be construed as limiting the scope of the invention.

EXAMPLE-1

Preparation of 5-(4-Isopropyloxy phenyl)-2E,4E-pentadienoic Acid Morpholine Amide of Formula 1 (n=2, x=O and Ar=4-isopropyloxy phenyl (i) Preparation of 1-(4-isopropyloxy phenyl) Ethanol of Formula 4 (R=C₃H₇)

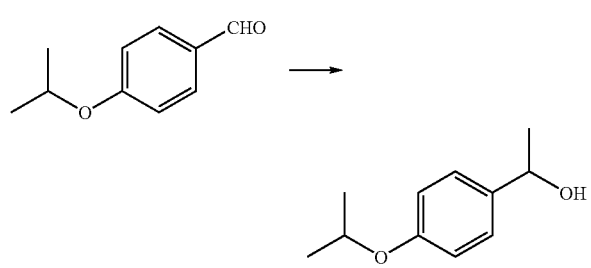

A solution of 4-isopropyloxy benzaldehyde of formula 5 (5 g, 30 mmol) in dry diethyl ether is slowly added to an ethereal solution of Grignard reagent prepared from magnesium metal (0.84 g, 35 mmol) and iodomethane (2.6 ml, 40 mmol) and the contents stirred for 1 hour at room temperature. After the completion of the reaction, the mixture is worked up by adding saturated aqueous solution of ammonium chloride (10 ml), followed by dilution with water (100 ml), separating the organic layer and extracting the aqueous layer with solvent ether (2×100 ml). The combined organic layer is washed with water (2×20 ml), dried over anhydrous sodium sulphate and concentrated in vacuo to yield 1-(4-isopropyloxy phenyl) ethanol, in a semisolid of general formula 4 in 92.5% yield.

(ii) Preparation of 3-(4-isopropyloxy phenyl)-2E-propenal of Formula 3, (R=C₃H₇)

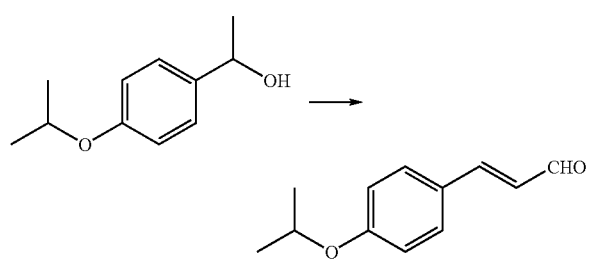

A solution of 1-(4-isopropyloxy phenyl) ethanol of formula 4 (4.8 g, 27 mmol) in dimethyl formamide (10 ml) is slowly added to phosphorus oxychloride (8 ml) in DMF (12 ml) with stirring at 0° C. The reaction mixture is stirred for 2 hours then allowed attaining room temperature followed by heating on an oil bath for 36 hour at 40° C. After the completion of the reaction as monitored by TLC, contents of the reaction mixture are poured into ice cold water (500 ml), neutralised with dilute alkali solution and saturated by adding sodium chloride. The aqueous portion is extracted with ethyl acetate (3×100 ml), organic layer washed with water, dried over anhydrous sodium sulphate and stripped off the solvent under vacuum to furnish crude product (4.8 g). It was purified by column chromatography over silica gel to yield a semisolid 3-(4-isopropyloxy phenyl)-2E-propenal of formula 3 (80%).

(iii) Preparation of 5-(4-isopropyloxy phenyl)-2E, 4E-pentadienoic Acid of Formula 2, (n=2 and R=C₃H₇)

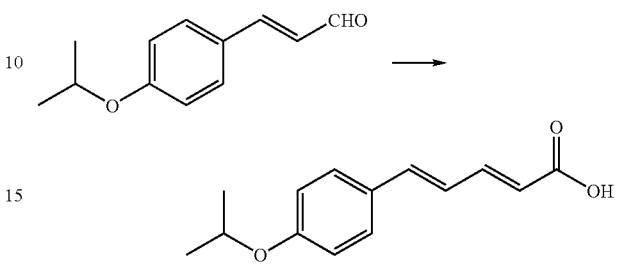

A mixture of triphenyl phosphine (4.7 g, 18 mmol) and ethyl bromoacetate (20 ml, 18 mmol) in anhydrous dimethoxy ethane is refluxed for 2 hour and to the intermediate thus formed is added 3-(4-isopropyloxy phenyl)-2E-propenal of formula 3 (2.5 g, 13 mmol), sodium hydride (0.5 g) in small proportions. The reaction mixture is continuously stirred for 72 hour at 60° C. The reaction mixture is then worked up by pouring onto ice cold water and extraction with dichloromethane (3×100 ml). The organic layer washed with water, dried over anhydrous calcium chloride and concentrated into vacuum. The crude 5-(4-isopropyloxy phenyl)-2E, 4E-pentadienoate obtained above is hydrolysed directly without purification in 10% methanolic potassium hydroxide solution on a water bath for 6 hour. On cooling, the contents diluted with water (200 ml) and extracted with dichloromethane (2×40 ml), the extracted aqueous portion is acidified with 2N hydrochloric acid solution. The resulting precipitate is filtered, washed with water and air dried to furnish crude acid (2.40 g, 80%). Crystallisation of the crude acid from ethyl acetate:benzene (19:1) furnished pure 5-(4-isopropyloxy-phenyl)-2E, 4E-pentadienoic acid of formula 2, m p 180° C.

(iv) Preparation of 5-(4-isopropyloxy phenyl)-2E, 4E-pentadienoic Acid Morpholine Amide of Formula 1 (n=2, x=O and R=C₃H₇)

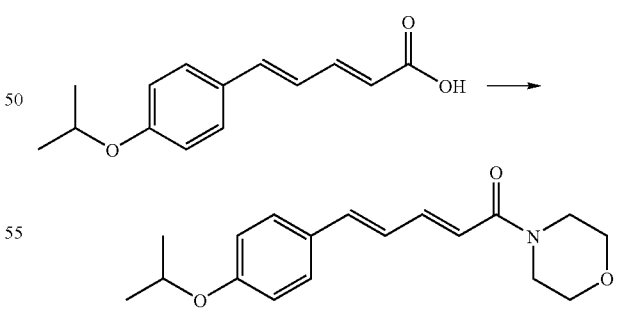

Freshly distilled thionyl chloride (0.5 ml) is added to a solution of 5-(4 isopropyloxy-phenyl)-2E, 4E-pentadienoic acid (1.4 g, 6 mmol) of formula 2 in dry dichloromethane and mixture is refluxed on a water bath for 1 hour. Solvent is removed from the acid chloride in vacuo along with excess of thionyl chloride. A solution of morpholine (0.6 ml, 7 mmol) in dichloromethane is added to the acid chloride prepared above and mixture stirred for 1 hour. After completion of the reaction, the organic layer is made free of excess of morpholine using dilute hydrochloric acid solution. The organic layer is washed with water, dried and concentrated under vacuum to furnish crude product (1.7 g, 94%), purified by crystallisation from ethyl acetate:hexane (9:1) to yield 5-(4-isopropyloxy phenyl)-2E, 4E-pentadienoic acid morpholine amide of formula 1.

Pale yellow crystals m.p. 134° C., analysed for $C_{18}H_{23}NO_3$ $^1$H NMR (200 M Hz) CDCl$_3$: δ 1.35 (6H, d, J=6 Hz, —(CH$_3$)$_2$—CH), 3.65 (8H, bs, N—(CH$_2$)$_2$—(CH$_2$)$_2$O—), 4.60 (1H, h, J=6 Hz, —OCH(CH$_3$)$_2$), 6.40 (1H, d, J=14.0 Hz, COCH=CH—), 6.65–7.05 and 7.20–7.85 (7H, 2× bs, Ar—H and olefinic H).

MS (E 1): M$^+$–1 at m/z 300 (35.6), 258 (11.1), 215 (18.5), 173 (100), 145 (18.2), 114 (24.0), 86 (22.6) and 70 (25.3).

EXAMPLE-2

Preparation of 5-(4-isopropyloxy phenyl)-2E,4E-pentadienoic Acid N-methyl Piperazine Amide of Formula 1 (n=2, x=N—CH$_3$ and R=C$_3$H$_7$)

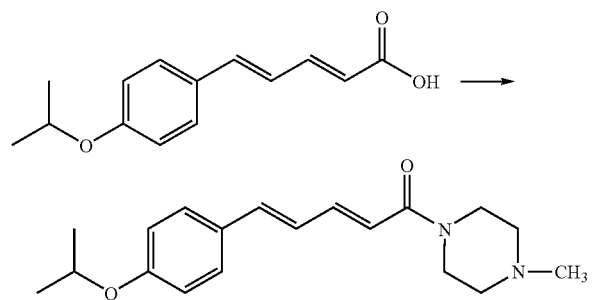

To a solution of 5-(-4-isopropyloxy phenyl)-2E, 4E-pentadienoic acid (0.93 g, 4 mmol) of formula 2 prepared by the method as described in example 1 (i–iii) in dry dichloromethane (40 ml) is added freshly distilled thionyl chloride (0.3 ml) and the mixture is refluxed on a water bath for 1 hr. thereafter the contents concentrated in vacuo and redissolved in dichloromethane (10 ml). A solution of N-methyl piperazine (0.4 ml, 4 mmol, in dichloromethane is added to acid chloride solution and the mixture is stirred for 2 hr at room temp. After the completion of the reaction, the contents are taken up in water (50 ml), the organic layer separated and the aqueous layer extracted with dichloromethane (2×15 ml). The combined organic layer is concentrated and the crude product purified by column chromatography on alumina (neutral) using chloroform: methanol (9:1) as eluent to give product, a semisolid (1.1 g, yield 93%), analysed for $C_{19}H_{26}N_2O_2$.

$^1$HNMR(200 MHz) CDCl$_3$ δ 1.31 (6H, d, J=6.05 Hz, (CH$_3$)$_2$—C) 2.31 (3H, S, —N—CH$_3$), 2.50 (4H, t, J=5.06, —N—(CH$_2$)$_2$), 3.71 (4H, m,—N—(CH$_2$)$_2$), 4.57 (1H, h, J=6.0 Hz, OCH—CH$_3$)$_2$), 6.67 (1H, d, J=15.3 Hz: CH=CH—CO), 6.85 (2H, d J=8.7 Hz, 2×Ar—H), 6.79–6.88 (1H, m, olefinic —H), 7.23–7.38 (1H, m olefinic —H), 7.44 (2H, d, J=8.7 Hz, 2×Ar—H) and 7.76 (1H, d, J=15.3 Hz, CH=CH—CO).

MS (E1): M$^+$–1 at m/z 313(16.9), 214(10.8), 170(12.6), 144(31.8), 118(21.9),70(74.3) and 57(100).

EXAMPLE-3

Preparation of 3-(4-isopropyloxy phenyl)-2E-propenoic Acid Morpholine Amide of Formula 1 (n=1, x=O and R=C$_3$H$_7$)

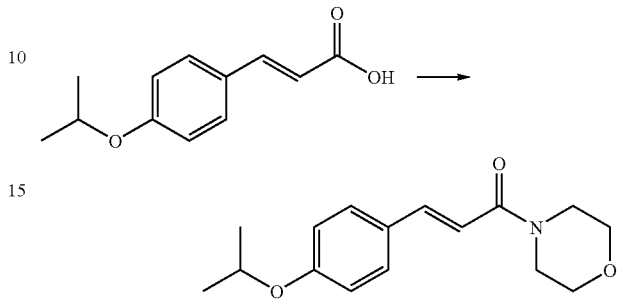

3-(4-isopropyloxy phenyl)-2E-propenoic acid of formula 2, n=1 and R=C$_3$H$_7$, (2.06, 10 mmol) a known compound in the art of synthesis is reacted with freshly distilled thionyl chloride (1.0 ml) in dry dichloromethane (15 ml) on a water bath for 1 hr. Solvent is removed in vacuo from the intermediate acid chloride along with the excess of thionyl chloride. A solution of morpholine (0.90 ml) in dry dichloromethane is added to the acid chloride prepared above and mixture stirred for 1 hr at room temp. After the completion of the reaction the organic layer is made free of excess of morpholine using dilute hydrochloric acid solution. The organic layer is washed with water, dried and concentrated under vaccum to furnish crude product which on crystallisation from ethyl acetate: hexane, furnished 3-(4-isopropyloxy phenyl)-2E-propenoic acid morpholine amide of general formula 2 where n=1, (m.p 98° C., Yield 2.66 g, 97%).

Creamish crystals m.p. 98° C., analysed for $C_{16}H_{21}NO_3$ $^1$H NMR (200 MHz) CDCl$_3$: δ 1.30 (6H, d, J=6 Hz, —(CH$_3$)$_2$—C), 3.70 (8H, s, O(CH$_2$)$_2$—(CH$^2$)$_2$—N—), 4.55 (1H, h, J=6 Hz, OCH—(CH$_3$)$_2$), 6.65 (1H, d, J=15.3 Hz, COCH=CH—), 6.85 (2H, d, J=8.5 Hz, 2×Ar—H), 7.40 (2H, d, J=8.5 Hz, 2×Ar—H) and 7.65 (1 H, d, J=15.3 Hz, CO—CH=CH).

MS (E1): M$^+$ at m/z 275 (28.8), 233 (12.7), 189 (34.6), 164 (14.1), 147 (100), 119 (30.7) and 91 (24.9).

EXAMPLE-4

Preparation of 3-(4-butyloxy phenyl)-2E-propenoic Acid Morpholine Amide of Formula 1 (n=1, x=O and R=C$_4$H$_9$)

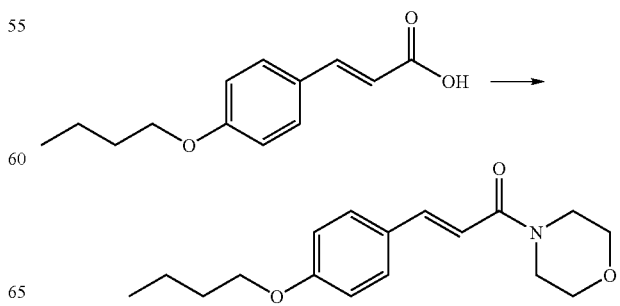

To a solution of 3-(4-butyloxyphenyl)-2E-propenoic acid (2.2 g, 10 mmol) in dichloromethane (40 ml) is added thionyl chloride (0.8 ml) and the resulting acid chloride made to react with morpholine (0.9 ml) as per procedure described in example 3 to give a solid (2.7 g, 90%) which is purified by crystallisation from ethyl acetate: n-hexane (9:1), mp 117° C., analysed for $C_{17}H_{23}NO_3$.

$^1$H NMR (200 MHz) CDCl$_3$: δ 1.0 (3H, t, J=6.5 Hz —CH$_2$—CH$_3$), 1.7 (2H, m, —CH$_2$—CH$_2$—CH$_3$) 1.8 (2H, m, —OCH$_2$—CH$_2$—CH$_2$), 3.76 (8H, bs, 2× —N(CH$_2$)$_2$—(CH$_2$)$_2$—O—), 4.03 (2H, t, J=6.5 Hz, —OCH$_2$—CH$_2$—), 6.75, (1H, d, J=15 Hz, —CH=CH—CO), 6.96 (2H, d, J=8 Hz, 2×Ar—H), 7.53 (2H, d, J=8 Hz, 2×Ar-H) & 7.78 (1H, d, J=15Hz, —CH=CH—CO).

MS(E1):M$^+$-1 at m/z 288(28.5), 203 (91), 146(100), 118(52),101(13) & 86(9.7).

EXAMPLE-5

Preparation of 3-(3,4-methylenedioxy phenyl)-2E-propenoic Acid N-methyl Piperazine Amide of Formula 1 (n=1, x=N—CH$_3$ and Ar=3', 4'-methylenedioxy phenyl.)

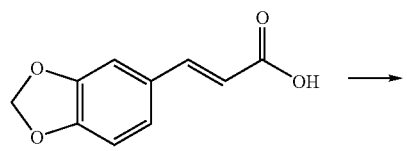

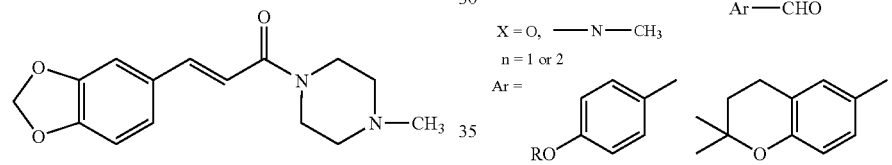

The N-methyl piperazine amide of 3-(3,4-methylenedioxy phenyl)-2E-propenoic acid is prepared from 3-(3,4-methylenedioxy phenyl) -2E-propenoic acid (1.92 g, 10 mmol), thionyl chloride (0.8 ml) and N-methyl piperazine (1.0 ml, 10 mmol) by the method described for example 2 to give solid (2.55 g, 91%), purified by crystallisation from chloroform: methanol (9:1), m.p 84° C., analysed for $C_{15}H_{18}N_2O_3$.

$^1$HNMR(200 Hz) CDCl$_3$; δ 2.33 (3H, s, —N—CH$_3$), 2.45 (4H, t, J=5.05 Hz, —N—(CH$_2$)$_2$),3.72 (4H, t, J=5.05 Hz, N—(CH$_2$)$_2$), 6.03 (2H, s, —OCH$_2$O—), 6.72 (1H, d, J=15.0 Hz, CH=CH—CO), 6.82 (1H, d, J=8.5 Hz, Ar—H), 6.95–7.23 (2H, m, 2×Ar—H) and 7.65 (1H, d, J=15.0Hz, CH=CH—CO).

MS(E1):M$^+$ at m/z 274(22.2) 174(17.7), 143(13.8), 115 (13.2), 70(100) and 57(83.3).

The Main Advantages of the Present Invention are:
1. The present invention provides novel substituted aryl alkenoic acid heterocyclic amides of general formula 1
2. Novel compounds with hot, pungent and spicy properties and synthetic substitutes for natural compounds and their process of preparation.
3. Novel compounds provided can be used as food additives.
4. The compounds in the present invention provides the pungency index in the range of $10^3$ to $10^7$ units as compared to the known pungent substances which have pungency index in the range of $10^3$ to $10^6$ units.
5. Novel compounds which may also be useful in the study of bioavailability enhancers and hepatic drug metabolism.
6. Novel compounds which may be useful as new test models in the development of anti-inflammatory and anti-arthritic drugs.

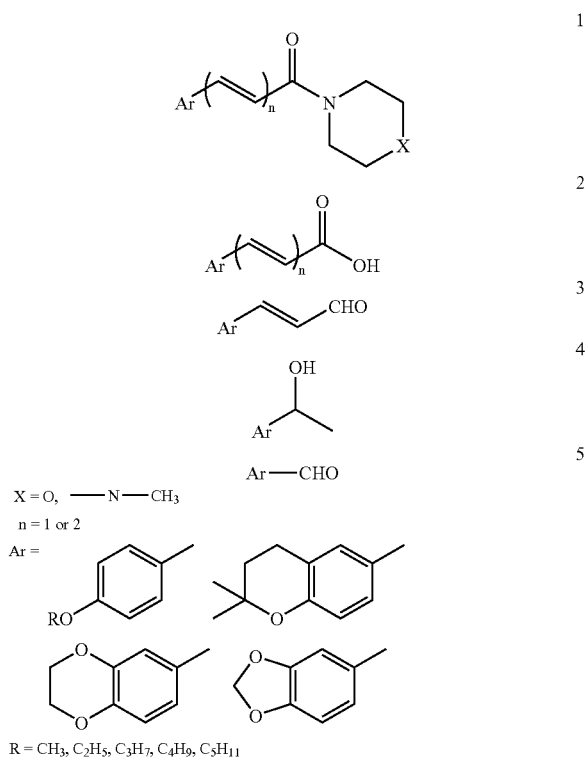

What is claimed is:

1. An arylalkenoic acid heterocyclic amide compound of the formula:

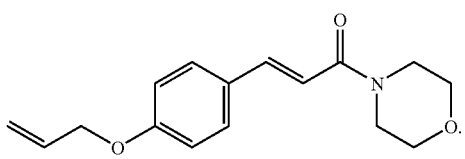

* * * * *